(12) United States Patent
Sarradon

(10) Patent No.: US 11,291,806 B2
(45) Date of Patent: Apr. 5, 2022

(54) ANGIOPLASTY DEVICE

(71) Applicant: Nexstep Medical, Dijon (FR)

(72) Inventor: Pierre Sarradon, Toulon (FR)

(73) Assignee: Nexstep Medical, Dijon (FR)

( * ) Notice: Subject to any disclaimer, the term of this patent is extended or adjusted under 35 U.S.C. 154(b) by 519 days.

(21) Appl. No.: 15/900,250

(22) Filed: Feb. 20, 2018

(65) Prior Publication Data

US 2018/0169391 A1 Jun. 21, 2018

Related U.S. Application Data

(63) Continuation of application No. 14/974,221, filed on Dec. 18, 2015, now Pat. No. 9,931,492, which is a continuation of application No. 13/130,022, filed as application No. PCT/FR2009/001326 on Nov. 18, 2009, now Pat. No. 9,248,263.

(30) Foreign Application Priority Data

Nov. 19, 2008 (FR) ........................... 0806472

(51) Int. Cl.
*A61M 25/10* (2013.01)
*A61M 25/00* (2006.01)
*A61M 25/09* (2006.01)
*A61M 5/00* (2006.01)
*A61B 17/22* (2006.01)

(52) U.S. Cl.
CPC .......... *A61M 25/104* (2013.01); *A61M 5/007* (2013.01); *A61M 25/007* (2013.01); *A61M 25/0032* (2013.01); *A61M 25/09* (2013.01); *A61B 2017/22001* (2013.01); *A61B 2017/22038* (2013.01); *A61B 2017/22062* (2013.01); *A61B 2017/22068* (2013.01); *A61M 25/0029* (2013.01); *A61M 2025/0004* (2013.01); *A61M 2025/109* (2013.01)

(58) Field of Classification Search
CPC .......... A61M 25/0029; A61M 25/0032; A61M 25/007; A61M 25/09; A61M 25/104; A61M 2025/0004; A61B 2017/22001; A61B 2017/22038; A61B 2017/22051; A61B 2017/22062; A61B 2017/22068; A61B 2017/22065; A61B 2017/22067; A61B 2017/22069

See application file for complete search history.

(56) References Cited

U.S. PATENT DOCUMENTS

| 4,545,390 A | 10/1985 | Leary |
| 4,748,984 A | 6/1988 | Patel |
| 4,763,654 A | 8/1988 | Jang |

(Continued)

FOREIGN PATENT DOCUMENTS

| EP | 1 897 584 A | 3/2008 | |
| EP | 2719418 A1 * | 4/2014 | ........ A61M 25/1036 |

(Continued)

*Primary Examiner* — Ashley L Fishback
(74) *Attorney, Agent, or Firm* — Chiesa Shahinian & Giantomasi

(57) ABSTRACT

The invention relates to an angioplasty device for treating stenoses or occlusions that facilitates the diagnosis and visualisation of the stenosis and the treatment control having a duct dedicated to the injection of the contrast product.

11 Claims, 7 Drawing Sheets

(56) References Cited

U.S. PATENT DOCUMENTS

| | | | |
|---|---|---|---|
| 4,777,951 A * | 10/1988 | Cribier | A61M 25/0023 |
| | | | 600/485 |
| 4,892,519 A | 1/1990 | Songer et al. | |
| 4,909,258 A | 3/1990 | Kuntz et al. | |
| 5,334,143 A * | 8/1994 | Carroll | A61M 29/02 |
| | | | 604/102.02 |
| 5,344,402 A | 9/1994 | Crocker | |
| 5,637,086 A * | 6/1997 | Ferguson | A61M 25/10 |
| | | | 604/509 |
| 5,921,957 A * | 7/1999 | Killion | A61M 25/0068 |
| | | | 604/96.01 |
| 6,090,096 A * | 7/2000 | St. Goar | A61M 25/10 |
| | | | 600/18 |
| 6,322,577 B1 | 11/2001 | McInnes | |
| 6,902,545 B2 * | 6/2005 | Bertolero | A61B 1/313 |
| | | | 604/102.03 |
| 2008/0058758 A1 * | 3/2008 | Ranchod | A61M 25/007 |
| | | | 604/508 |
| 2009/0036831 A1 | 2/2009 | Howat | |
| 2010/0268159 A1 * | 10/2010 | Engel | A61M 25/1018 |
| | | | 604/99.03 |

FOREIGN PATENT DOCUMENTS

| | | |
|---|---|---|
| FR | 2 533 130 A | 3/1984 |
| WO | WO 2007/132447 A2 | 11/2007 |
| WO | WO 2007/132447 A3 | 11/2007 |

\* cited by examiner

ANGIOPLASTY DEVICE

CROSS REFERENCE TO RELATED APPLICATIONS

This application is a continuation of U.S. patent application Ser. No. 14/974,221 filed Dec. 18, 2015, which is a continuation of U.S. patent application Ser. No. 13/130,022 filed May 18, 2011, now U.S. Pat. No. 9,248,263 issued Feb. 2, 2016, which is a 371 of PCT/FR2009/001326 filed on Nov. 18, 2009, published on May 27, 2010 under publication number WO 2010/058103 A, and claims priority benefits to French patent application number 0806472 filed Nov. 19, 2008, the entire disclosures of which are incorporated herein by reference.

TECHNICAL FIELD OF THE INVENTION

The invention relates to an angioplasty device to be introduced into a conduit of the human body, which conduit is preferably a blood vessel, so as to permit the local widening of the conduit. This device is particularly useful for treating occlusions or stenoses of the blood vessels.

PRIOR ART

To treat a stenosis or an occlusion of a blood vessel, an angioplasty device can be used that is composed of a rod on which an inflatable balloon is fixed. Such a device is described in EP 1 897 584, for example. This device comprises a rod which is provided with an inflatable balloon and in which two conduits are formed. The first conduit is designed to receive a flexible guide wire for guiding the path of the device in the vessel as far as the zone that is to be treated, while the second conduit is in fluidic communication with the balloon, thus permitting the injection of a pressurized fluid into the balloon, in this particular case physiological saline, if appropriate mixed with an iodine contrast agent.

To fit this device in place, a contrast agent can be injected into the blood vessel in order to locate the stenosis. A guide wire is then introduced into the vessel to be treated in order to make it easier to introduce the angioplasty device into the area of the stenosis. A guide wire and a method for using it are described in the document FR 2 533 130, for example.

The angioplasty device is then introduced around the guide wire in such a way that the guide wire is located in the first conduit. Once the balloon has been introduced into the area of the stenosis, a pressurized fluid is injected into the balloon with the aid of the second conduit. The inflation of the balloon makes it possible to widen the blood vessel in the area of the stenosis. It is then once again necessary to visualize the blood vessel in order to check that the stenosis has indeed been rectified. To do this, the balloon catheter is withdrawn and replaced by an angiography catheter which has a multi-perforate end and which is positioned in line with or upstream from the treated lesion. The guide is then withdrawn and an iodine contrast agent is injected into the lumen of the angiography catheter. If a new angioplasty is required, the guide can be mounted again on the angiography catheter, and the catheter can then be withdrawn and replaced by the balloon catheter.

Alternatively, to make matters simpler, the guide wire can be withdrawn and the contrast agent can be injected though the lumen freed by the guide wire, as long as the diameter of this guide lumen is sufficient, given that the contrast agent is viscous. In cases where the stenosis has not been totally rectified, the balloon has to be repositioned at the location where the blood vessel is narrowed. To do this, a guide wire must be re-introduced into the first conduit in order to permit the repositioning of the balloon in the narrowed area of the blood vessel. This maneuver of repositioning the balloon can be repeated several times if the stenosis has not been completely rectified.

Thus, the treatment of a stenosis, or of an occlusion, involves a succession of treatment phases, during which the balloon is inflated, and of visualization phases, during which a contrast agent is injected. Between each treatment phase and visualization phase, the operator performing the injection must either withdraw the balloon and replace it by an angiography catheter or must withdraw the guide wire in order to use the freed channel. This successive introduction and withdrawal of the guide wire into and out of the first conduit is time-consuming and awkward for the surgeon to do.

Another disadvantage of these techniques is that the distribution of the contrast agent in the blood vessel always takes place in the direction of flow of the blood, with the result that if the vessel comprises branches between the injection point and the location of the lesion, some of the contrast agent is uselessly diffused into the adjoining vessels.

In addition, in the devices of the prior art, the contrast agent is injected into the blood vessel with the aid of the first conduit, such that it is injected into the whole of the blood vessel. Large amounts of contrast agent are therefore injected into the patient's blood, and this can have adverse consequences for the health of the patient.

DISCLOSURE OF THE INVENTION

It is an object of the invention to overcome the disadvantages of the prior art by making available a percutaneous transluminal angioplasty device with which it is possible to visualize the blood vessel without having to perform any additional maneuver. It is also an object of the invention to improve the quality of visualization while at the same time reducing the amounts of contrast agent that are injected into the patient's blood.

To this end, a first aspect of the invention concerns an angioplasty device comprising:
   a guide wire to be inserted into a blood vessel,
   a flexible tubular body extending along a longitudinal axis between a proximal end and a distal end and having a proximal part, which includes the proximal end, and a distal part, which includes the distal end, the tubular body comprising:
      an inflatable balloon arranged radially about the tubular body in the distal part;
      a first leaktight internal conduit extending parallel to the longitudinal axis at least in the distal part, so as to permit the insertion of the guide wire into the first conduit and the sliding of the tubular body along the guide wire;
      at least a second internal conduit extending parallel to the longitudinal axis and opening out, on the one hand, at the proximal end and, on the other hand, into the balloon (5), in such a way as to permit the injection of a fluid into the balloon;
in which angioplasty device the tubular body additionally comprises:
   one or more injection orifices situated in the distal part;
   a third internal conduit opening out, on the one hand, at the proximal end and, on the other hand, into the injection orifice or orifices, in such a way as to permit the injection of a contrast agent through the one or more injection orifices when the guide wire is in the first conduit.

The angioplasty device thus comprises a third conduit and at least one infusion orifice situated in the distal part of the tubular body. This injection orifice permits the injection of a contrast agent into the blood without the need to withdraw the guide wire. The angioplasty device can therefore be repositioned very easily and very quickly. The injection orifice is preferably located less than 5 cm from the balloon. In cases where the tubular body comprises several injection orifices, the injection orifice farthest from the balloon is preferably located less than 5 cm from the balloon.

This device can therefore be used for the diagnosis of stenoses or occlusions, and it can also be used for their treatment. This device also makes it possible to check that the inflating of the balloon has indeed rectified the occlusion or the stenosis, without the need to remove the guide wire.

This device therefore serves as a visualization probe and, at the same time, as an instrument for treating the stenoses or occlusions.

Moreover, the contrast agent is injected locally by virtue of the infusion orifice situated in proximity to the balloon, which permits very precise visualization of the area of interest through injecting a small amount of contrast agent into the patient's blood.

The quality of visualization of the contrast agent can also be improved by distributing infusion orifices radially about the tubular body, downstream and upstream from the balloon, by which means it is possible to obtain a satisfactory distribution of the contrast agent, irrespective of the direction of flow of the blood.

The second conduit is leaktight in order to ensure that the fluid for inflating the balloon does not enter the patient's blood.

Advantageously, according to one embodiment, the first conduit is circular and has a diameter substantially equal to that of the guide wire. In this way, the conduit and the guide wire are in good contact and, by this means, the angioplasty device is more easily guided by the guide wire.

According to another embodiment, the first conduit is open radially on the third conduit in order to form a single conduit, the diameter of the single conduit being greater than the external diameter of the guide wire in the proximal part of the tubular body, the diameter of the single conduit being substantially equal to the external diameter of the guide wire in the distal end of the tubular body. In this embodiment, the infusion orifices are preferably situated upstream from the portion of the single conduit whose diameter is substantially equal to that of the guide wire, such that the contrast agent can be injected without the need to withdraw the guide wire, since the contrast agent exits through the infusion orifices that are situated upstream from the conduit portion that is narrower. This embodiment also allows the contrast agent to be injected at high pressure by withdrawing the guide from the distal part in such a way as to obtain a supplementary injection orifice. Moreover, during the passage of the tubular body around the guide wire, friction is minimized. This embodiment is also advantageous in terms of industrial production of the tubular body, since only two conduits have to be formed in the tubular body, instead of the three conduits present in the preceding embodiments.

The cross section of the third conduit must be chosen in such a way as to satisfy two contradictory conditions: it must be as large as possible in order to permit a rapid rate of injection of the contrast agent, of which the viscosity is high, and it must also be small enough to ensure that the device as a whole has the smallest possible diameter.

According to different embodiments:
each conduit can be leaktight, in order to control the flow of the fluids in the device;
the tubular body can comprise a plurality of injection orifices in fluidic communication with the third conduit, the injection orifices being distributed radially about the tubular body; this distribution of the injection orifices permits a better distribution of the visualization medium in the area to be treated;
the one or more injection orifices include at least one downstream injection orifice situated downstream from the balloon;
the one or more injection orifices include at least one upstream injection orifice situated upstream from the balloon; the distribution of the injection orifices upstream and downstream from the balloon makes it possible to improve the visualization of the stenosis, irrespective of the direction of flow of the blood;
the first, second and third conduits can be concentric; in this case, the first conduit is at the center in order to provide a good hold of the guide wire, the second conduit surrounds the first conduit, and the third conduit surrounds the first and second conduits in order to permit better visualization of the area in which the balloon is situated; this arrangement can save space, such that the diameter of the tubular body as a whole is reduced and, as a result, the insertion of the angioplasty device into the blood is easier;
the first, second and third conduits are arranged side by side, which makes production of the device easier;
the proximal end of the tubular body is provided with three connector pieces, each connector piece being attached in a leaktight manner to one of the conduits;
the first conduit is open radially on the third conduit, which reduces the number of conduits to be formed and makes them easier to produce, especially when the conduits are produced by drilling the tubular body;
the first conduit opens out, on the one hand, at the proximal end and, on the other hand, at the distal end, which allows the guide wire to pass from one end to the other;
the first conduit opens out, on the one hand, at an intermediate position between the proximal end and the distal end and, on the other hand, at the distal end, which facilitates the manipulations between the tubular body and the guide wire.

The invention also relates to a tubular body according to one of the embodiments described above.

BRIEF DESCRIPTION OF THE FIGURES

Other features and advantages of the invention will become clear from the following description and by reference to the attached figures, in which.

For greater clarity, identical or similar elements are designated by identical reference signs in all of the figures.

DETAILED DESCRIPTION OF AN EMBODIMENT

Figure 1:
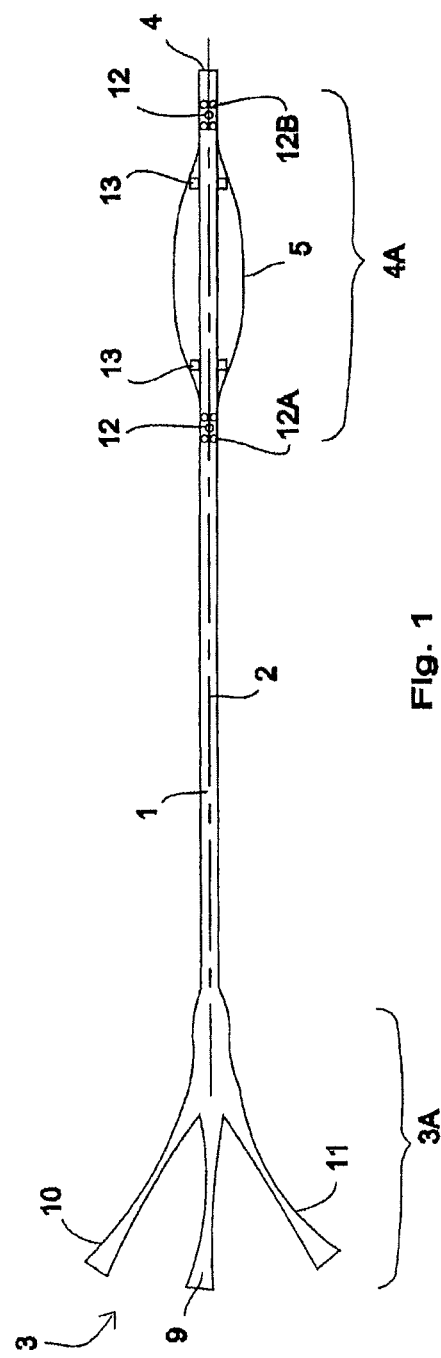
FIG. 1 shows a schematic view of an angioplasty device according to a first embodiment of the invention.

The angioplasty device shown in FIG. 1 comprises a tubular body 1 made of a flexible and biocompatible material, especially a synthetic material, and extending along a longitudinal axis 2 between a proximal end 3 and a distal end 4. The tubular body additionally comprises a proximal part 3A, which includes the proximal end 3, and a distal part 4A, which includes the distal end 4. The tubular body 1 is provided, in its distal part 4A, with an inflatable balloon 5, which radially surrounds the tubular body.

The tubular body 1 additionally comprises injection orifices 12, which are formed in the wall of the tubular body and which are arranged radially upstream 12B and downstream 12A from the inflatable balloon 5. These injection orifices 12 are arranged in proximity to the inflatable balloon. The terms upstream and downstream refer to the direction of flow of the fluid in the angioplasty device.

Figure 2:
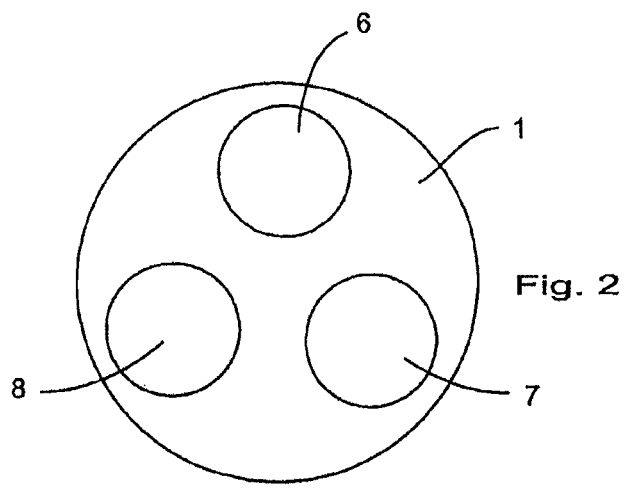
FIG. 2 shows a cross-sectional view of the tubular body of the angioplasty device from FIG. 1.

Three conduits 6, 7, 8, which are shown in section in FIG. 2, pass through the tubular body. The three conduits 6, 7 and 8 extend parallel to the longitudinal axis. The first conduit 6 extends along the entire length of the tubular body, such that it connects the distal and proximal ends 3, 4 of the tubular body. The first conduit 6 is of circular cross section and has an internal diameter substantially equal to the external diameter of the guide wire that will allow the angioplasty device to be placed in the vein. Thus, the angioplasty device is better guided by the guide wire. The proximal end 3 is additionally provided with a connector piece 9, which is attached to the first conduit 6. The guide wire is introduced into the first conduit 6 through the connector piece 9.

The second conduit 7 connects the proximal end 3 of the tubular body to the inflatable balloon 5 in a leaktight manner. The proximal end 3 is provided with a second connector piece 10, which is attached in a leaktight manner to the second conduit. The connector piece 10 is designed to be attached to a device for injecting a pressurized fluid into the second conduit 7 in order to inflate the balloon. This pressurized fluid is advantageously a mixture of physiological saline and contrast agent.

The third conduit 8 connects the proximal end 3 of the tubular body to the infusion orifices 12. The proximal end 3 is additionally provided with a third connector piece 11, which is connected in a leaktight manner to the third conduit 8. The third conduit 8 permits the injection of a contrast agent into the blood vessel in order to visualize the narrowing of the blood vessel to be treated and in order to monitor the latter after the angioplasty.

Moreover, to make it easier to position the balloon at the location of the narrowing, in particular when the balloon is not inflated, a positioning ring 13 is placed in the balloon. This positioning ring 13 is detectable, just like the contrast agent, by X-ray. In a preferred embodiment, the tubular body can comprise two positioning rings, each of these rings being placed at the limit of the balloon so as to permit detection of the latter.

Figure 3:
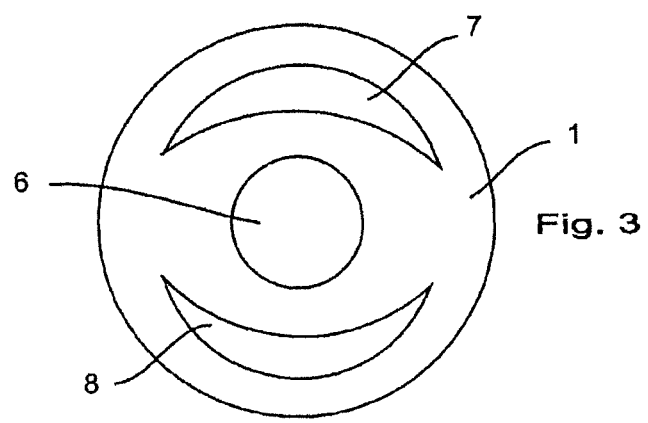
FIG. 3 shows a cross-sectional view of the tubular body of an angioplasty device according to a second embodiment of the invention.
Figure 4:
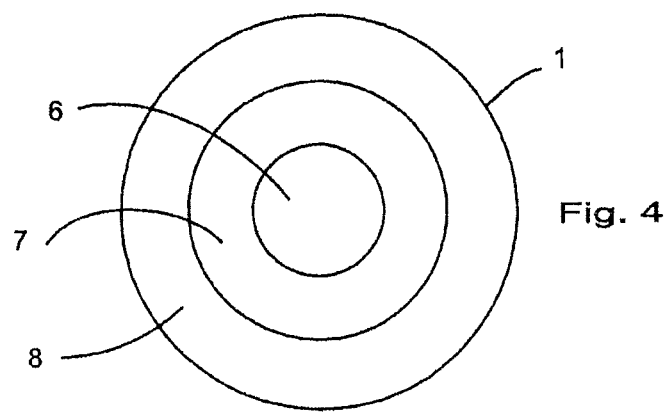
FIG. 4 shows a cross-sectional view of the tubular body of an angioplasty device according to a third embodiment of the invention.

The arrangement of the conduits inside the tubular body can vary, as can be seen in FIGS. 3 to 7. In FIGS. 3 and 4, the first conduit 6 has a circular cross section with a diameter substantially equal to that of the guide wire that will be introduced into this first conduit 6. In the arrangement in FIG. 3, the second and third conduits 7 and 8 are arranged as crescents around the first conduit, whereas in the arrangement in FIG. 4 the three conduits 6, 7 and 8 are of circular cross section and are concentric. The first conduit 6 is at the center of the tubular body and is surrounded by the second conduit 7, which is itself surrounded by the third conduit 8.

Figure 5:
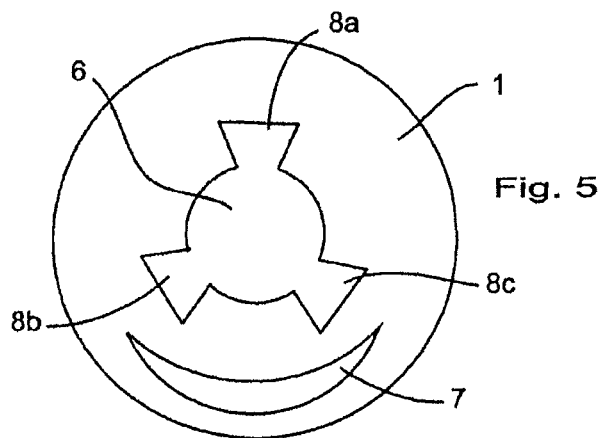
FIG. 5 shows a cross-sectional view of the tubular body of an angioplasty device according to a fourth embodiment of the invention.
Figure 6:
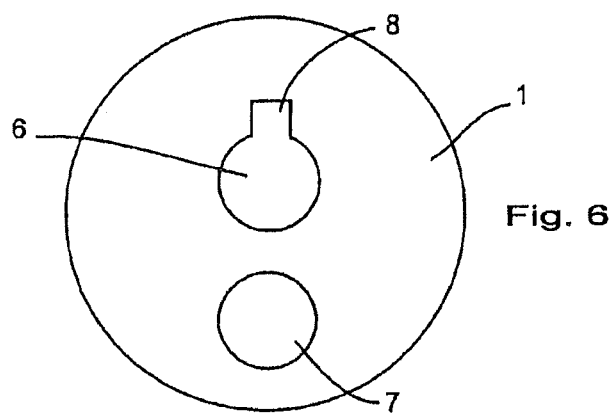
FIG. 6 shows a cross-sectional view of the tubular body of an angioplasty device according to a fifth embodiment of the invention.
Figure 7:
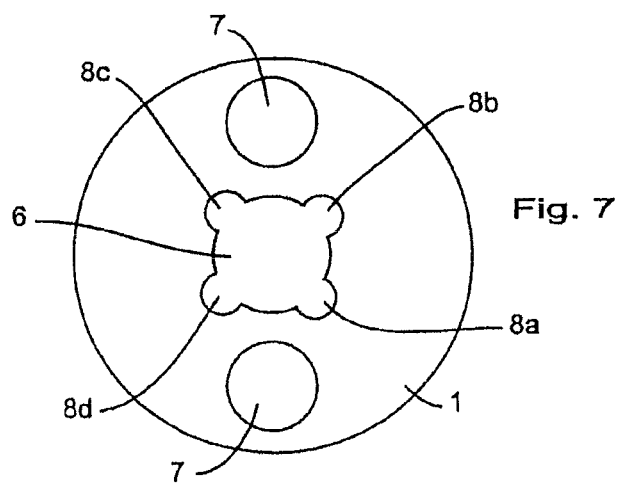
FIG. 7 shows a cross-sectional view of the tubular body of an angioplasty device according to a sixth embodiment of the invention.

FIGS. 5 to 7 show another arrangement in which the first conduit 6 is open radially on the third conduit 8. In these embodiments, the first conduit still has a circular cross section with a diameter substantially equal to that of the guide wire so as to permit efficient guiding of the tubular body around the guide wire. To save space and reduce the number of holes to be made, the first conduit 6 is open radially on the third conduit 8. In FIG. 5, the third conduit is in fact composed of three conduits 8a, 8b, 8c, which communicate with the first conduit and are distributed radially about the first conduit. This arrangement is particularly advantageous when the infusion orifices 12 are distributed radially about the tubular body, since it permits a good distribution of the infusion product between the infusion orifices 12. Likewise in FIG. 7, the third conduit is in fact composed of four conduits 8a, 8b, 8c, 8d, which communicate with the first conduit and are distributed radially about the first conduit. These embodiments additionally allow the third conduit to be dimensioned according to the amount of contrast agent to be injected, but also according to the viscosity thereof.

Figure 8:
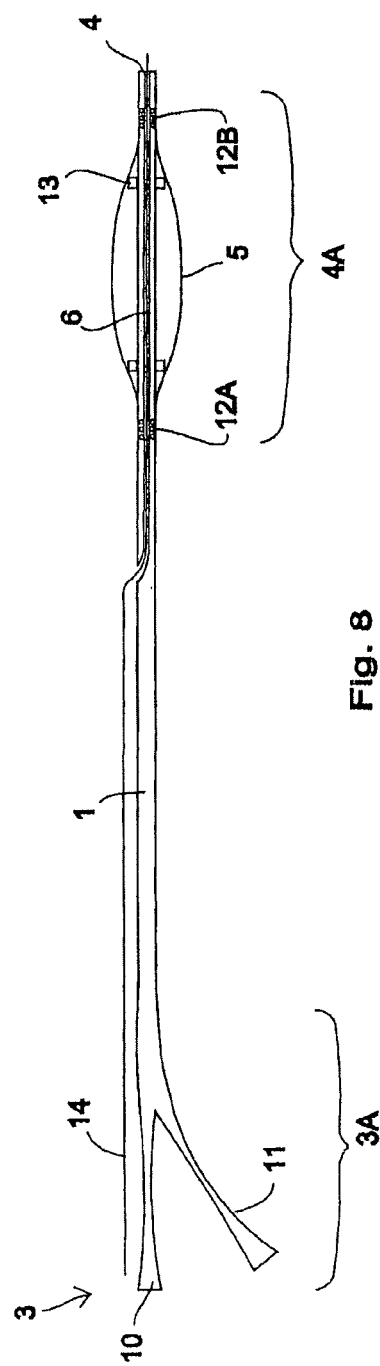
FIG. 8 shows a schematic view of an angioplasty device according to a seventh embodiment of the invention.

FIG. 8 shows an angioplasty device according to another embodiment of the invention. In this embodiment, the tubular body 1 comprises only two conduits in its proximal part 3A, namely the second and third conduits, and it comprises three conduits in its distal part 4A. In this part where the tubular body comprises only two conduits, the guide wire 14 is external to the tubular body 1, whereas in the distal part, where the tubular body comprises three conduits, the guide wire passes through the first conduit.

Figure 9:
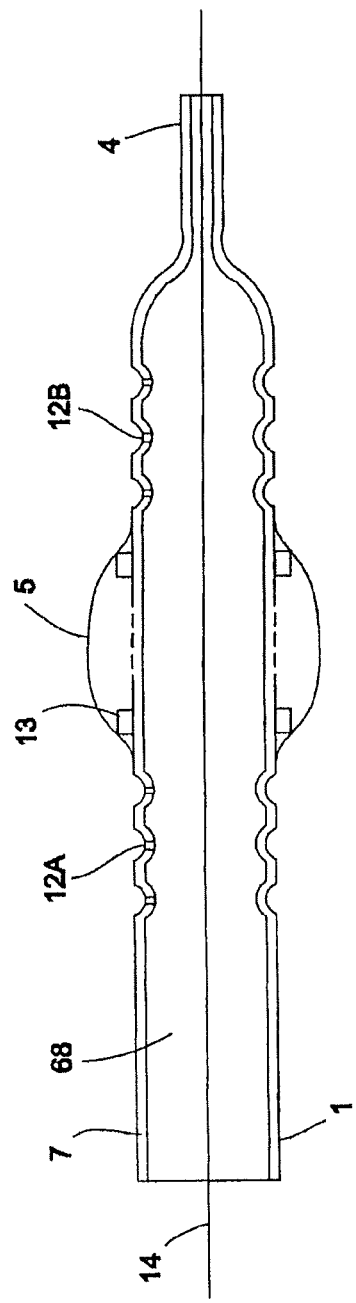
FIG. 9 shows a schematic view of an angioplasty device according to an eighth embodiment of the invention.
Figure 10:
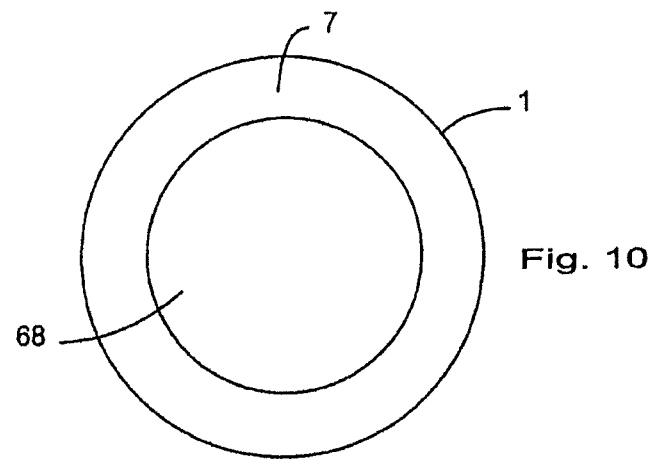
FIG. 10 shows a cross-sectional view of the proximal part of the angioplasty device from FIG. 9.
Figure 11:
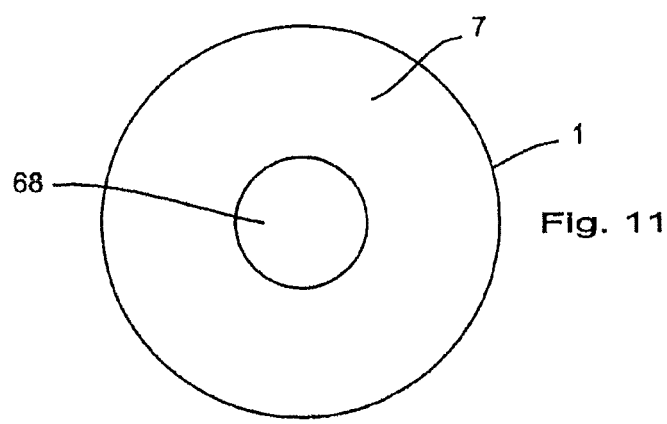
FIG. 11 shows a cross-sectional view of the end of the distal part of the angioplasty device from FIG. 9.

FIGS. 9, 10 and 11 show an angioplasty device according to another embodiment, in which the first conduit 6 and the third conduit 8 are merged and form a single conduit 68. This single conduit 68 has a diameter greater than the external diameter of the guide wire 14 along the entire length of the tubular body, except for the end of the distal part 4, where the single conduit has a diameter substantially equal to the external diameter of the guide wire 14. A cross section of the proximal part of the tubular body of this angioplasty device is shown in FIG. 10, and a cross section of the end of the distal part of the tubular body of this angioplasty device is shown in FIG. 11. The second conduit 7 and the single conduit are concentric in this embodiment. The infusion orifices 12 are preferably situated upstream from the portion of the single conduit 68 whose diameter is equal to that of the tubular body, so as to make it easier for the contrast agent to pass through the single conduit 68, without having to withdraw the guide wire. This arrangement permits the injection of a pressurized contrast agent. In addition, it reduces the friction between the guide wire 14 and the conical conduit 68.

Figure 12:
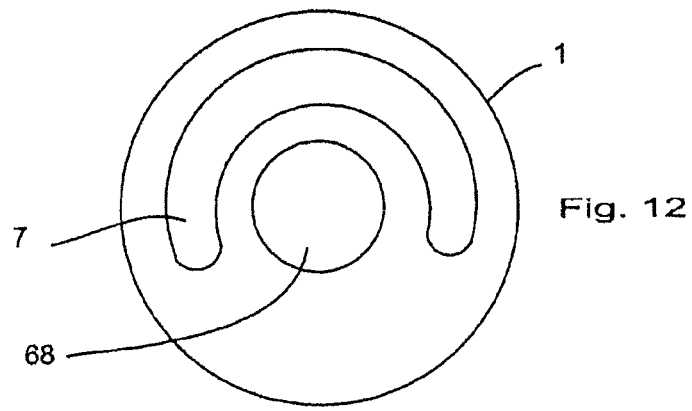
FIG. 12 shows a cross-sectional view of the proximal part of a ninth embodiment of the invention.

FIG. 12 shows a variant of the embodiment from FIG. 9, in which variant the single conduit 68 and the second conduit are not concentric.

Figure 13:
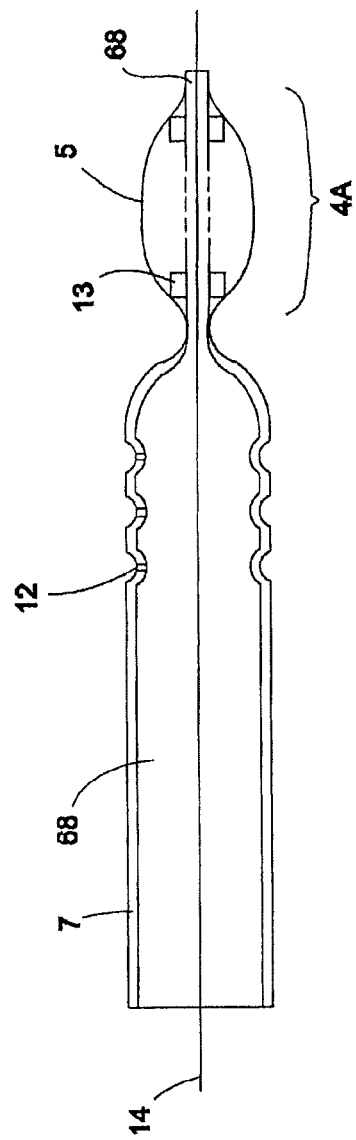
FIG. 13 shows a schematic view of an angioplasty device according to a second embodiment.

FIG. 13 shows a variant of the embodiment from FIG. 9. In this embodiment, the first conduit 6 and the third conduit 8 are merged and form a single conduit 68. This single conduit 68 has a diameter greater than the external diameter of the guide wire 14 along the entire length of the tubular body, except for the distal part 4A, where the single conduit 68 has a diameter substantially equal to the external diameter of the guide wire 14 in the distal part 4A of the tubular body. In addition, in this embodiment, the balloon 5 is positioned at the distal end 4A of the tubular body, around the part of the single conduit 68 having a diameter substantially equal to the diameter of the guide wire 14. In this way, the tubular body has substantially the same diameter along its entire length. In addition, this diameter is relatively small.

The treatment of a stenosis with the aid of the angioplasty device in FIG. 1 will now be described.

In a first step, the operator inserts a catheter into the vein to be treated and injects a contrast agent, for example iodine, into the blood vessel to be treated. By virtue of this contrast agent, the operator can observe the blood vessel by radiography and is thus able to locate the stenosis that is to be treated. The operator then introduces the guide wire into the vessel to be treated and thereafter inserts the angioplasty device into the blood vessel by sliding the first conduit over the guide wire. The guide wire facilitates the introduction of the angioplasty device despite the flexibility and the length of the latter.

The operator places the balloon in the area of the narrowing with the aid of the marker ring 13, which is radio-labeled. Once the balloon has reached the narrowed segment of the blood vessel, the operator inflates the balloon with the aid of the second conduit 7. The atheromatous deposits narrowing the vessel are then compressed against the walls of the blood vessel, thereby permitting an increase in the diameter of the internal lumen of the vessel. Once this maneuver has been performed, the balloon is deflated, again with the aid of the second conduit 7.

Then, with the aid of the third conduit, the operator injects a contrast agent into the patient's blood without having to carry out the manipulations necessary in the prior art. The injection of this contrast agent allows the operator to visualize the blood vessel after the inflation of the balloon, so as to be able to check that the narrowed segment has indeed been rectified. In cases where this narrowed segment has not been totally rectified by the first inflation, the operator can move the balloon in order to reposition it in the area of the remaining narrowed portion. This remaining narrowed portion is detected with the aid of the contrast agent. Once the balloon has been repositioned, the operator can re-inflate the balloon. He can then once again check whether this maneuver has been successful. The operator can repeat these widening/checking maneuvers as many times as is necessary and can do so without having to carry out any additional manipulation, which saves him considerable time and avoids possible incidents during the manipulation. In addition, the contrast agent is injected locally, by which means the practitioner is able to clearly visualize the area of interest without excessive contrast agent having to be injected into the patient's blood.

Of course, the invention is not limited to the above illustrative embodiments, and various modifications or variations can be envisioned. For example, other arrangements of the three conduits can be envisioned. It is also conceivable to add a fourth conduit in the tubular body, for example for injecting medicaments or active substances into the blood.

Moreover, the tubular body can either be a solid cylinder in which three conduits are drilled or can be in the form of a cylindrical outer wall which surrounds the three conduits.

The invention claimed is:

1. An angioplasty device configured for local widening of a narrowed segment of an internal lumen of a blood vessel including atheromatous deposits on walls of the blood vessel, comprising:
   a guide wire configured to be inserted into the blood vessel;
   a flexible tubular body extending along a longitudinal axis between a proximal end and a distal end, wherein the flexible tubular body comprises a proximal part that includes the proximal end, and a distal part that includes the distal end, the tubular body further comprising:
      an inflatable angioplasty balloon arranged radially about the tubular body in the distal part, wherein the angioplasty balloon is configured such that inflation of the angioplasty balloon in the narrowed segment of the blood vessel causes the internal lumen of the blood vessel to widen, the atheromatous deposits to compress against the walls of the blood vessel, and the stenosis to be durably rectified;
      a leaktight first internal conduit extending parallel to the longitudinal axis at least in the distal part, which permits insertion of the guide wire into the first conduit and sliding of the tubular body along the guide wire;
      a second internal conduit extending parallel to the longitudinal axis and opening out, on the one hand, at the proximal end and, on the other hand, into the angioplasty balloon, in such a way as to permit the injection of a fluid into the angioplasty balloon to inflate the angioplasty balloon;
      a third internal conduit opening out at the proximal end and into several injection orifices situated in the distal part, each less than 5 cm away from the angioplasty balloon,
      wherein the first, second and third conduits are leaktight with respect to one another, and wherein the third conduit has a cross-sectional dimension based on an amount and viscosity of a contrast agent to be injected therethrough and into a patient's blood.

2. The angioplasty device of claim 1, wherein the injection orifices are distributed radially about the tubular body.

3. The angioplasty device of claim 1, wherein the injection orifices include at least one downstream injection orifice situated between the angioplasty balloon and the distal end.

4. The angioplasty device of claim 1, wherein the injection orifices include at least one upstream injection orifice situated between the proximal part and the angioplasty balloon.

5. The angioplasty device of claim 1, wherein the first, second, and third conduits are concentric.

6. The angioplasty device of claim 1, wherein the first, second, and third conduits are arranged side by side.

7. The angioplasty device of claim 1, wherein the first conduit has a circular cross section and has a diameter approximately equal to that of the guide wire.

8. The angioplasty device of claim 1, wherein the proximal end of the device is provided with three connector pieces, each connector piece attached in a leaktight manner to one of the conduits.

9. The angioplasty device of claim 1, wherein the first conduit opens out, on the one hand, at the proximal end and, on the other hand, at the distal end.

10. The angioplasty device of claim 1, wherein the first conduit opens out, on the one hand, at an intermediate position between the proximal end and the distal end and, on the other hand, at the distal end.

11. An angioplasty device configured for local widening of a narrowed segment of an internal lumen of a blood vessel including atheromatous deposits on walls of the blood vessel, comprising:
- a guide wire configured to be inserted into a blood vessel,
- a flexible tubular body extending along a longitudinal axis between a proximal end and a distal end, wherein the flexible tubular body comprises a proximal part that includes the proximal end, and a distal part that includes the distal end, the tubular body further comprising:
  - an inflatable angioplasty balloon arranged radially about the tubular body in the distal part, wherein the angioplasty balloon is such that an inflation of the angioplasty balloon in the narrowed segment of the blood vessel causes the internal lumen of the blood vessel to widen, the atheromatous deposits to compress against the walls of the blood vessel and the stenosis to be durably rectified;
  - a first internal conduit extending parallel to the longitudinal axis at least in the distal part, the first conduit having a diameter substantially equal to that of the guide wire over an entire length of the first internal conduit so as to permit the insertion of the guide wire into the first conduit and the sliding of the tubular body along the guide wire;
  - a second internal conduit extending parallel to the longitudinal axis and opening out, on the one hand, at the proximal end and, on the other hand, into the angioplasty balloon, in such a way as to permit the injection of a fluid into the angioplasty balloon to inflate the angioplasty balloon;
  - a third internal conduit opening out at the proximal end and into one or more injection orifices situated in the distal part, each of the one or more injection orifices being located less than 5 cm away from the angioplasty balloon, the third conduit having a cross-section dimension based on an amount and a viscosity of a contrast agent to be injected therethrough and into a patient's blood, wherein the first, second and third conduit are leaktight with respect to one another.

* * * * *